(12) United States Patent  
Chan (10) Patent No.: US 10,180,442 B2  
(45) Date of Patent: Jan. 15, 2019

(54) SAMPLE CONSUMABLE AND LOADER (71) Applicant: DNA Medicine Institute, Inc., Cambridge, MA (US)

(72) Inventor: Eugene Y. Chan, Boston, MA (US)

(73) Assignee: DNA Medicine Institute, Inc., Cambridge, MA (US)

( * ) Notice: Subject to any disclaimer, the term of this patent is extended or adjusted under 35 U.S.C. 154(b) by 301 days.

(21) Appl. No.: 14/645,388

(22) Filed: Mar. 11, 2015

(65) Prior Publication Data

US 2015/0260745 A1 Sep. 17, 2015

Related U.S. Application Data

(60) Provisional application No. 61/952,014, filed on Mar. 12, 2014.

(51) Int. Cl.
*G01N 35/10* (2006.01)
*B01L 3/00* (2006.01)
*B67D 1/00* (2006.01)
*B05B 11/00* (2006.01)

(52) U.S. Cl.
CPC ......... *G01N 35/10* (2013.01); *G01N 35/1011* (2013.01); *B01L 3/502715* (2013.01); *B01L 2200/025* (2013.01); *B01L 2200/0684* (2013.01); *B01L 2300/0841* (2013.01); *B05B 11/0054* (2013.01); *B65D 2583/005* (2013.01); *B67D 1/0078* (2013.01); *G01N 2035/1039* (2013.01); *G01N 2035/1051* (2013.01)

(58) Field of Classification Search
CPC .................. G01N 35/1011; G01N 2035/1039
USPC ................................................. 222/325, 420
See application file for complete search history.

(56) References Cited

U.S. PATENT DOCUMENTS

| | | | | |
|---|---|---|---|---|
| 6,623,613 | B1 * | 9/2003 | Mathies | B01L 3/5025 204/450 |
| 2008/0118399 | A1 * | 5/2008 | Fleming | A61B 10/0045 422/68.1 |
| 2009/0060793 | A1 * | 3/2009 | Eickhoff | G01N 35/10 422/400 |
| 2010/0240142 | A1 * | 9/2010 | Saiki | B01L 3/50273 436/164 |
| 2014/0374299 | A1 * | 12/2014 | Tsai | B01L 3/50855 206/438 |

FOREIGN PATENT DOCUMENTS

CN 203616170 U * 5/2014 ............... G01N 1/14

* cited by examiner

*Primary Examiner* — R. A Smith  
*Assistant Examiner* — John M Royston  
(74) *Attorney, Agent, or Firm* — Danielson Legal LLC (57) ABSTRACT

A sample consumable that carries a microvolume of sample to a sample loader. The consumable is precisely aligned utilizing a double-alignment feature to the loader. The loader is based on a crank-slider geometry and allows for simple, one-handed operation for the user. Overall, the consumable and sample loader increase reproducibility of in-line sample loading and offers ease-of-use.

13 Claims, 6 Drawing Sheets

SAMPLE CONSUMABLE AND LOADER

CROSS-REFERENCE TO RELATED APPLICATIONS

The present application claims the benefit of U.S. provisional application No. 61/952,014, filed on Mar. 12, 2014, the entire disclosure of which is incorporated by reference as if set forth in its entirety herein.

STATEMENT REGARDING FEDERALLY SPONSORED RESEARCH OR DEVELOPMENT

This invention was made with government support under National Institutes of Health Grant #5 R44 HL099092-03. The government has certain rights in the invention.

FIELD

The present invention relates to sample loading for miniature fluidic systems, and particularly to the macro-to-micro sample loading problem.

BACKGROUND

Sample loading into biological instruments and devices with fluidic systems currently requires large sample volumes, typically greater than 100 µL. In biology and science, samples are precious and often there is a desire to use as small a volume as possible. This is exemplified in the "world-to-chip" problem, where microfluidic devices are capable of handling volumes <1 µL, but it is difficult to load a sample of that size into the device. The "world" can include biological, chemical, and clinical samples that are derived from experiments, blood, and other biological fluidics. The ability to fabricate increasingly smaller channels in glass, fused silica, and other materials through photolithography further emphasizes the importance of solving this problem.

This sample loading problem is present in flow-based systems, such as flow cytometers, where a moving fluid flow carries a sample to a laser detection region for analysis. Current methods of sample loading for a flow cytometer, or similar types of flow-based instruments, include utilizing a sample withdrawal tube for "sipping" the sample. This approach typically requires 200 µL of sample, of which only 50 µL may be withdrawn and analyzed. While the sample injection tube is flushed between uses, there is still the possibility of cross-contamination. This leads to a waste of 150 µL of sample, which for fear of contamination cannot be returned to its original source.

Lab-on-valve devices also require sample injection. In these systems, a rotating valve allows selection among the different types of samples introduced into the system. Sample introduction is typically accomplished using syringes attached to the inlet ports. Microvolume syringes exist but they are typically expensive for single-use applications.

Sample injection is also important in various types of chromatography. In chromatography systems, after the sample is injected by the syringe, there is sometimes a rotary diaphragm valve that is utilized to load precise volumes of samples into flow based systems. A certain sample volume is introduced by the syringe. This sample fills a section of channel. The diaphragm valve is rotated to bring the filled channel to connect with a carrier fluid and the entrance to the column. Movement of the carrier fluid displaces the sample. This approach allows a precise amount of volume to be delivered to the system. The diaphragm valve approach for sample loading thus requires a syringe for sample injection and a rotary valve for fluid metering, The presence or absence of bubbles at either end of the sample can impact the loading profile of the sample into the system. The desired loading profile for a sample can take one of several configurations: bubble in front, bubble in back, bubble on both sides, and no bubbles. The bubble interface introduces plug flow on that side of the sample, whereas no bubble leads to a stretched sample as it goes through the system. No bubble on both sides leads to a long transit time for the sample through the system and the greatest amount of sample dilution. A long transit time may not be desirable if the sample analysis time is to be short. Conversely, bubbles on both sides may not be desirable if some sample dilution is required. The ideal sample loading may be a bubble on one end, preferably the back end of the sample, such that the front end has a parabolic profile and some sample dilution.

A diversity of methods can be utilized to address this problem, including inserting a capillary in-line with tubing, using U-shaped consumables, dummy consumables, in-line loaders, and variations thereof. One can also exclude a bubble based on inserting a pin into the capillary as well as making one end of the capillary contact first prior to the other end. These approaches are complex and further simplicity is desirable.

SUMMARY

Embodiments of the present invention provide an improved approach to sample loading using a consumable with a sample region that can be readily inserted in-line into a custom sample loader. Various embodiments of the consumable include a double-alignment feature, tab, air pocket, and precise capillary volume, among other features.

The sample loader has two halves that form a fluid seal when closed. When open, there is a slot for the consumable with the sample to be loaded in-line with the system. Both the consumable and the sample loader have specific geometries that either eliminate or introduce a bubble into the loaded sample, thus permitting the creation of a desired loading profile. Furthermore, embodiments of the sample loader feature geometries that allow for one-handed operation, facilitating the one-handed introduction of the consumable into the system.

In one aspect, the present invention concerns a consumable for loading a sample. The consumable comprises a body, an inner alignment feature disposed within the body for aligning the consumable with a loader, and an outer alignment feature for aligning the consumable with the loader. The body may be fabricated from a transparent material.

In one embodiment, the body is cylindrical and the outer alignment feature is the cylindrical shape of the body. In one embodiment, the consumable further comprises a tab that extends from the body. In one embodiment, the consumable may comprise an air pocket connecting the capillary and the loading region.

In one embodiment, the consumable further includes a capillary for holding a sample and a loading region connected to the capillary for loading the capillary, wherein the loading region is substantially larger than the capillary. The capillary may be concentric with the inner alignment feature and the outer alignment feature. The capillary may be tapered.

In another aspect, the present invention relates to a loader for receiving a consumable holding a sample. The loader includes a slider plunger, a door crank, and a rod that aligns to the outside surface of the loaded consumable. The loader may be configured for one-handed operation. The consumable may be cylindrical.

In one embodiment, the loader further comprises a latch and the slider plunger is spring loaded, the actuation of the latch causing the slider plunger to open the door crank for loading a consumable. In one embodiment, the loader further comprises a receptacle for the consumable and a gasket disposed therein, and when the loader is closed the slider plunger forms a seal with the back of the consumable and the front end of the consumable forms a seal with the gasket. In one embodiment, the loader further comprises a needle for penetrating a capillary in the consumable.

In yet another aspect, the present invention relates to a method for analyzing a sample. The method includes loading the sample into a capillary disposed within a consumable, loading the consumable into a loader, and closing the loader, thereby forming a seal between a slider plunger and the back of the consumable and a seal between a gasket and the front of the consumable. The loading and closing may be performed one-handed. The consumable may be cylindrical.

In one embodiment, the method further comprises actuating a latch to cause the slider plunger to open a door crank for loading the consumable. Loading the consumable into a loader may comprise placing the consumable in contact with at least one guide rail. The consumable may be loaded by the handling of a tab on the consumable.

DETAILED DESCRIPTION

Overview

A consumable should be easily handled by all users. The user should be able to easily hold onto it and be able to load it into the system. There should a region for holding the sample in the consumable. The filling of this sample region should be easy and avoid unintentional air bubbles. A consumable should be readily loaded into the system and form fluid seals reproducibility.

Embodiments of the consumable in accord with the present invention address these different complexities and requirements by having a double-alignment feature, internal tapered capillary, defined sample volume, defined air pocket, clear material, and a tab grip. The double-alignment feature allows precision alignment of the consumable in the system, allowing for failsafe sample loading. The internal tapered capillary has a defined volume so that fluid forms a positive convexity at the front end of the capillary, allowing for a bubble-free seal at the front end. There is a defined air pocket at the back of the sample based on geometric features of the consumable. The consumable is made from a clear or translucent material, allowing for visualization of the sample. It also has a tab grip for easy handling.

The consumable addresses several major challenges of sample loading: bubble in back and no bubble in front, ergonomic design, proper sample filling, reproducible sample loading, and ease-of-use. The particular loading profile, bubble in back and no bubble in front, is important because of the dilution and transit time experienced by the analysis time.

The sample loader accepts the consumable and has an inlet and outlet for fluid. The sample loader has a minimum of two different states, one with and one without the consumable. In the absence of the consumable, the sample loader makes a seal and fluid is able to pass through the system. This is the closed state of the sample loader. When the consumable is present, the sample loader is able to direct fluid through the consumable, displacing the sample, and thus moving the sample into the system. Other states of the loader can include the open state, which can allow the consumable to be loaded into the system.

The sample loader should have one-handed operation, i.e., that the user can open the loader and load the consumable with one hand. This is important because the user may be in a non-laboratory environment that prevents use of their other hand. This means that the sample loader should remain open by itself during loading so that the consumable can be loaded into the system. Once the consumable is loaded, the loader should be able to be closed with one hand.

The loader also needs to have precision alignment features to accept the consumable. These alignment features should be robust and lead to reproducible sample loading. The alignment should have a place for locating the consumable as well as alignment to the inlets and outlets of the sample loader.

Another aspect of the sample loader in accord with the present invention is based on a crank-slider mechanism. A crank-slider is a mechanical means of translating rotational motion into linear motion. Embodiments of the invention utilize this mechanism coupled with a spring-based mechanism that seals around the consumable.

There is a latch on the crank-slider loader that allows it to be closed. When the latch is pressed, the system is spring-loaded and the door opens automatically. The open door allows the user to insert the consumable in a one-handed method. The crank-slider utilizes metal shafts for precision alignment of the consumable with the consumable receptable. An o-ring mates to the back of the consumable and the consumable is sealed to a flat gasket at the front.

One aspect of the invention concerns a method for loading a small microvolume of sample in-line with tubing and a fluidic system. The consumable holds the sample and the mechanical loader receives the consumable. The consumable transfers the sample to the loader. The loader forms fluid seals on both sides of the sample and allows pressure driven flow to move the sample into the system. Depending on the geometry of both the consumable and the loader, bubbles can be eliminated or added to have the desired loading profile.

Embodiments of the present invention can introduce a sample in-line with a flow path in a way that is low-cost and easy-to-use. The consumable and loader are manufacturable using existing production methods, such as injection molding, extrusion, stamping, or other commercially-available methods.

Consumable

Figure 1:
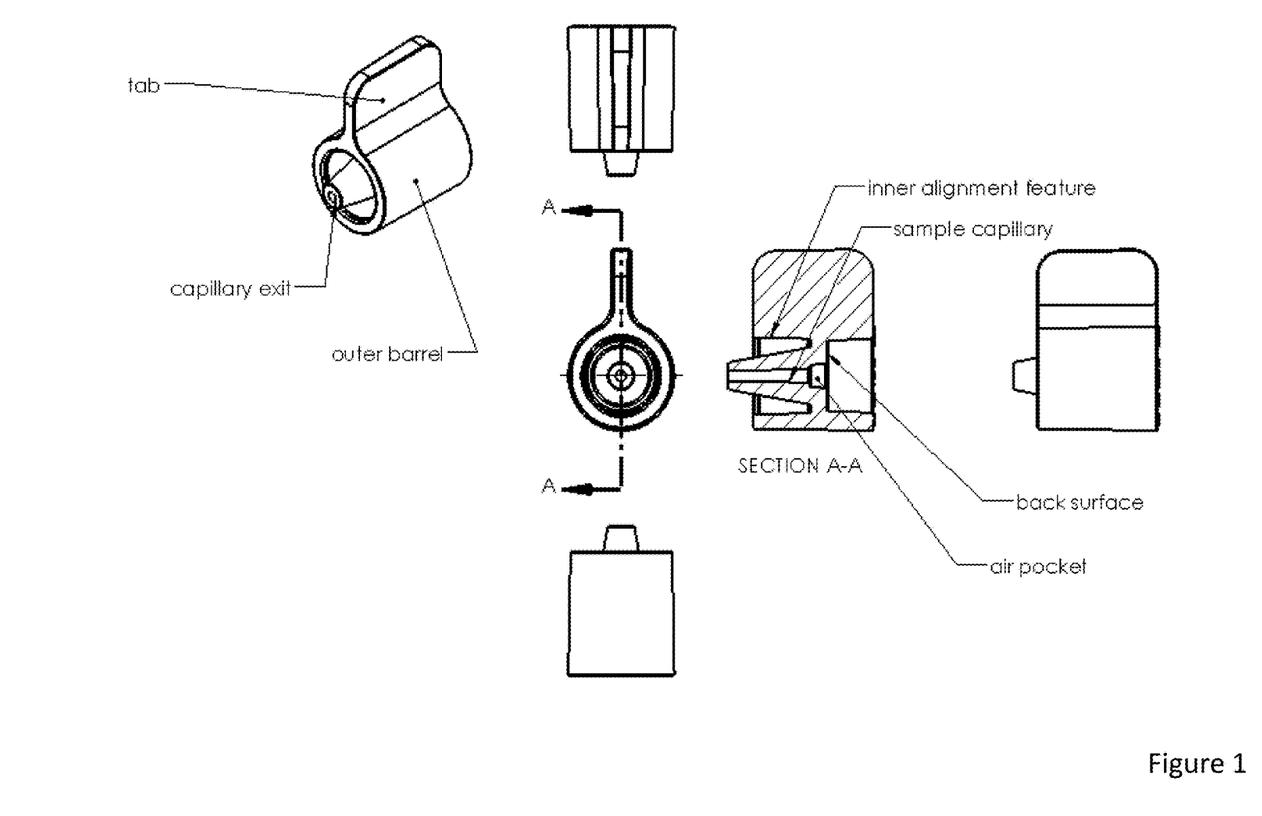
FIG. 1 illustrates an exemplary consumable in accord with the present invention.
Figure 2:
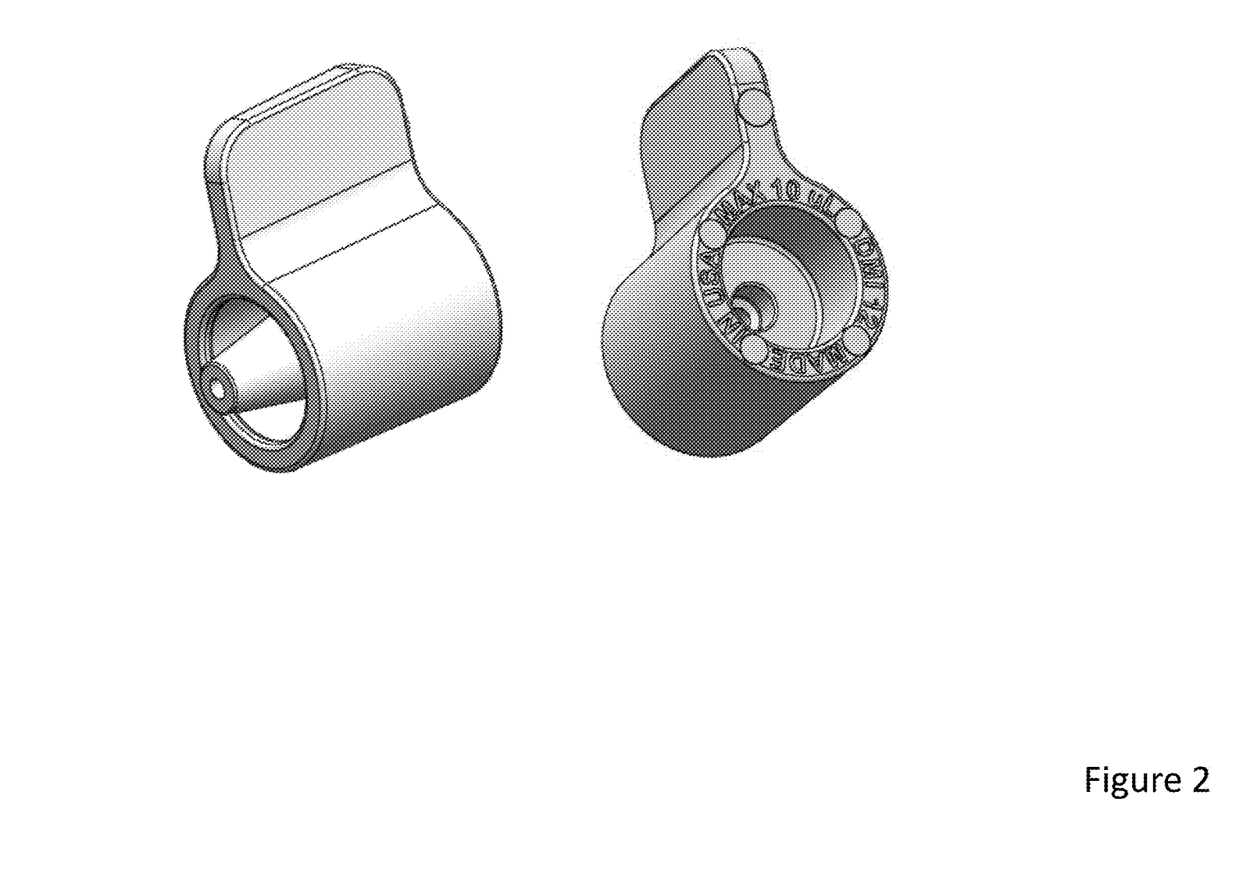
FIG. 2 shows the consumable of FIG. 1 in a three-dimensional view.
Figure 3:
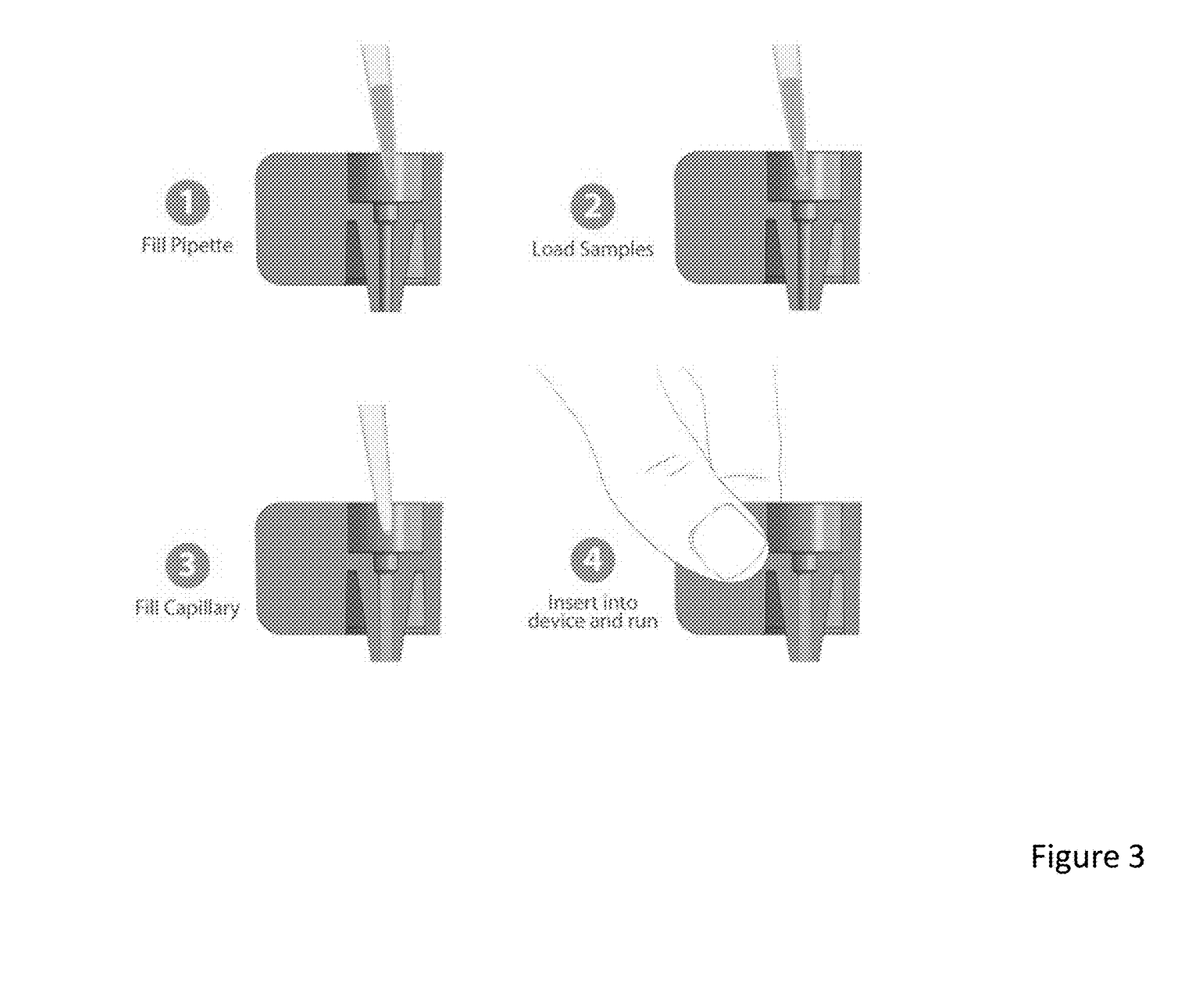
FIG. 3 shows one method for loading a sample into the consumable of FIGS. 1 and 2.

One embodiment of the consumable is shown in FIGS. 1-3. With reference to FIG. 1, the consumable has a tab for holding, a capillary for holding the sample, an area for a back air pocket, and a double-alignment feature. The main body is cylindrical with a tab for easy handling and ergonomics. The material is transparent to allow visualization of the sample. The container allows for fluid sealing on both ends to prevent leaks during operation.

The consumable's double-alignment feature guides its loading directly in-line with the sample loader. Precision alignment with the loader is important since the tolerance to alignment ranges from ±0.005" to ±0.010". Inability to precisely align the consumable with the loader can lead to leaks and loss of sample. These tolerances can be difficult to attain, especially when each loader and consumable is mass manufactured.

The double-alignment feature is implemented in two parts. The outer barrel of the consumable is cylindrical. This feature allows it to sit on guide rails on the loader. A cylindrical shape allows the user to insert it from a variety of positions and, regardless, it will self-align with the loader's cylindrical receptacle. The inner barrel of the consumable is also cylindrical and may have a taper to allow for a precise fit. The inner barrel of the consumable mates with the loader's cylindrical receptacle.

As shown in FIG. 1, the inner capillary channel is concentric with the double-alignment feature. This allows the capillary to be directly lined up with the gasket and the exit needle of the sample loader. It is important that the exit barrel of the capillary form a seal around the exit needle, otherwise leaks will occur. The reproducibility of alignment needs to be very high, and the exit needle size is typically 28 gauge (0.01425"). The size of this needle dictates the precision of the alignment.

The consumable may have a tab for easy handling. The tab feature is ergonomic and allows the user to hold onto the consumable readily. By holding onto the tab feature, the user can easily pipette the sample into the inner capillary barrel of the consumable. This allows for ready visualization of the filling capillary. The tab is molded from the plastic housing. Its size should accommodate the diversity of finger sizes, from extra small to extra large.

A preferred loading profile of the sample in flow cytometry applications is no bubble in front and a bubble in the back. This allows for an analysis time of approximately 1-2 minutes for a 10 μL sample. No bubbles on both ends would lead to a much longer analysis time and therefore is not desired. Bubbles on both sides would lead to not enough sample dilution and too fast a transit time. In order to attain this loading profile, the consumable needs to have appropriate features. The first is an area for an air pocket on the consumable. This is accomplished by having a larger recessed area on the back pocket of the consumable. The capillary fill area is separate from this. When the loader's o-ring seal forms on the back of the capillary, it forms around the larger recessed area. Thus, when fluid is passed through the consumable to drive the sample into the system, the air pocket resides on the back of the sample. Therefore, a consumable with a recess for forming an air pocket helps ensure that a bubble forms on the back of the sample.

Forming a bubble-free interface can be accomplished in a variety of ways. A first method is to design the capillary volume to be less than the actual fill volume so that fluid forms a positive convexity at the front end of the capillary. For instance, if the pipetted sample is 10 μL, then the capillary volume can be 9.5 μL, or 0.5 μL less than the pipetted volume. The excess volume forms a positive convexity at the front end of the capillary. When this consumable and sample is loaded into the loader that has been primed, it will form a bubble-free seal at the front end of the consumable.

An alternate method of forming a bubble-free seal at either end of the capillary is to have a short section of a blunt needle protrude into the capillary. The insertion of the needle into the capillary displaces any potential air at the ends of the capillary, allowing for a robust, bubble-free seal. The length of the needle protrusion and its gauge determines how much air can be displaced. This volume can be adjusted by changing the needle gauge and its protrusion length. The blunt needles will need to be primed prior to being inserted to ensure that there is no air in the needles. In all cases, failure to attain the desired type of seal will compromise the integrity of the diagnostic test.

The consumable has two ends where it can form fluid tight seals. The front end of the consumable presses against a gasket. The spring-based loader presses and seals against the back of the consumable. Overall, the spring-based force along the axis of the consumable allows seals to be formed at both ends. It is important that the seal is on-axis so that fluid passes through the seals and the capillary without blockage. This means that the alignment mechanism must be precise for the consumable and the loader.

The consumable's capillary volume is preferably defined to range from 5-100 μL. Volumes outside this range can also be accommodated. The volume is based on the capillary fill volume within the capillary. Capillary diameters in the range from 0.020" to 0.060" are typical but it can be larger or smaller to fully accommodate the desired volume. The capillary can be tapered or flared to accommodate a certain desired volume. If tapered or flared, the capillary walls can be smooth so that no bubbles are formed. The taper can be consistent with the fill direction, i.e. the larger end should be the entrance of the fluid.

The material for the consumable can be a clear or translucent material to allow visualization of the sample. This could include polycarbonate, polymethylmethacrylate, PETG, or other similar material. The surface properties of the plastic can allow the sample to appropriately wet the walls of the capillary. This is based on a desirable contact angle with the desired fluid to be analyzed. The surface finish of the material can be smooth, particularly on the inside of the capillary to allow smooth filling. Manufacture of the consumable should be free of particles, oils, or residues.

Sample Loader

Figure 4:
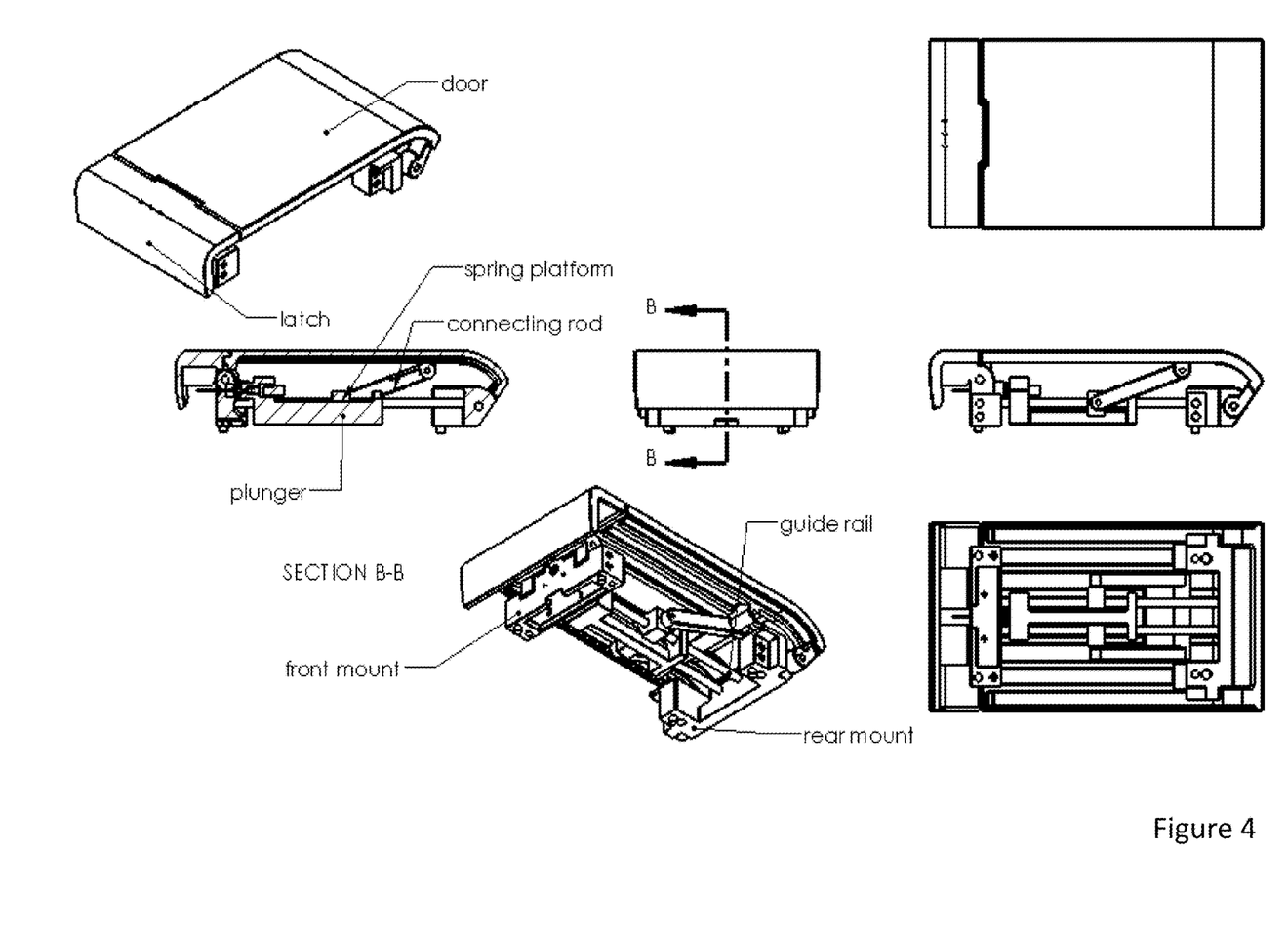
FIG. 4 illustrates an exemplary crank-slider sample loader in accord with the present invention.
Figure 5:
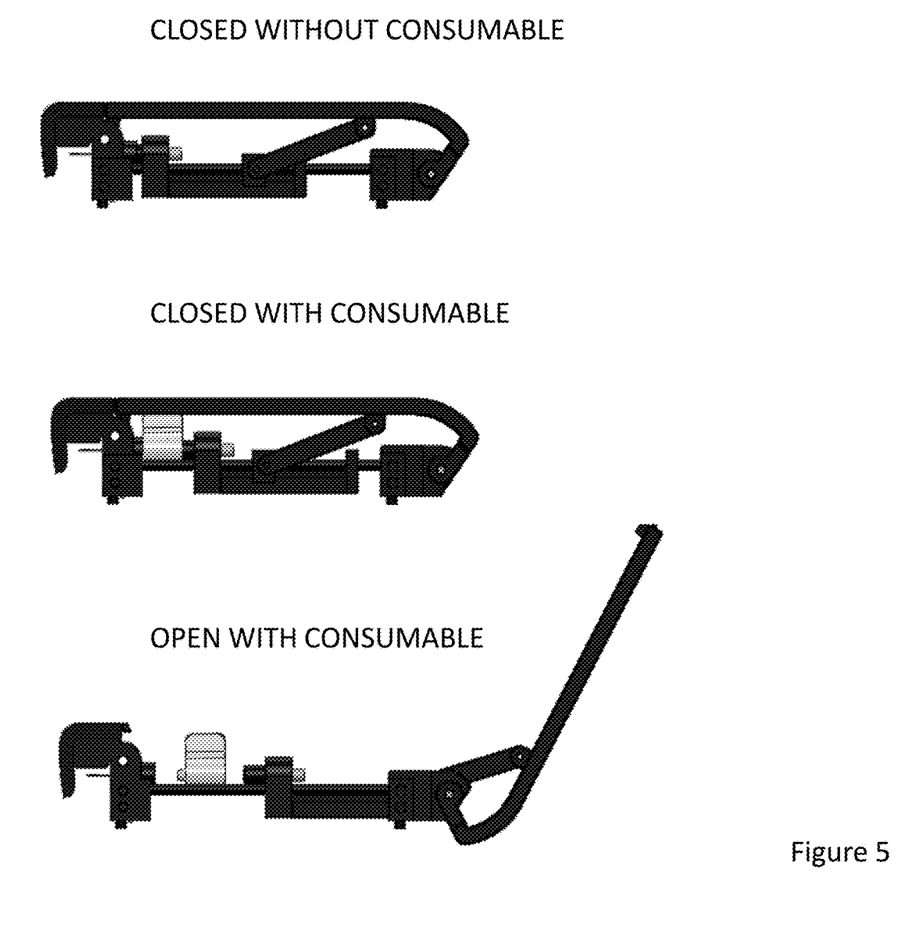
FIG. 5 presents the sample loader of FIG. 4 in side profile, showing the three different states of the loader: closed without consumable, closed with the consumable, and open with the consumable.
Figure 6:
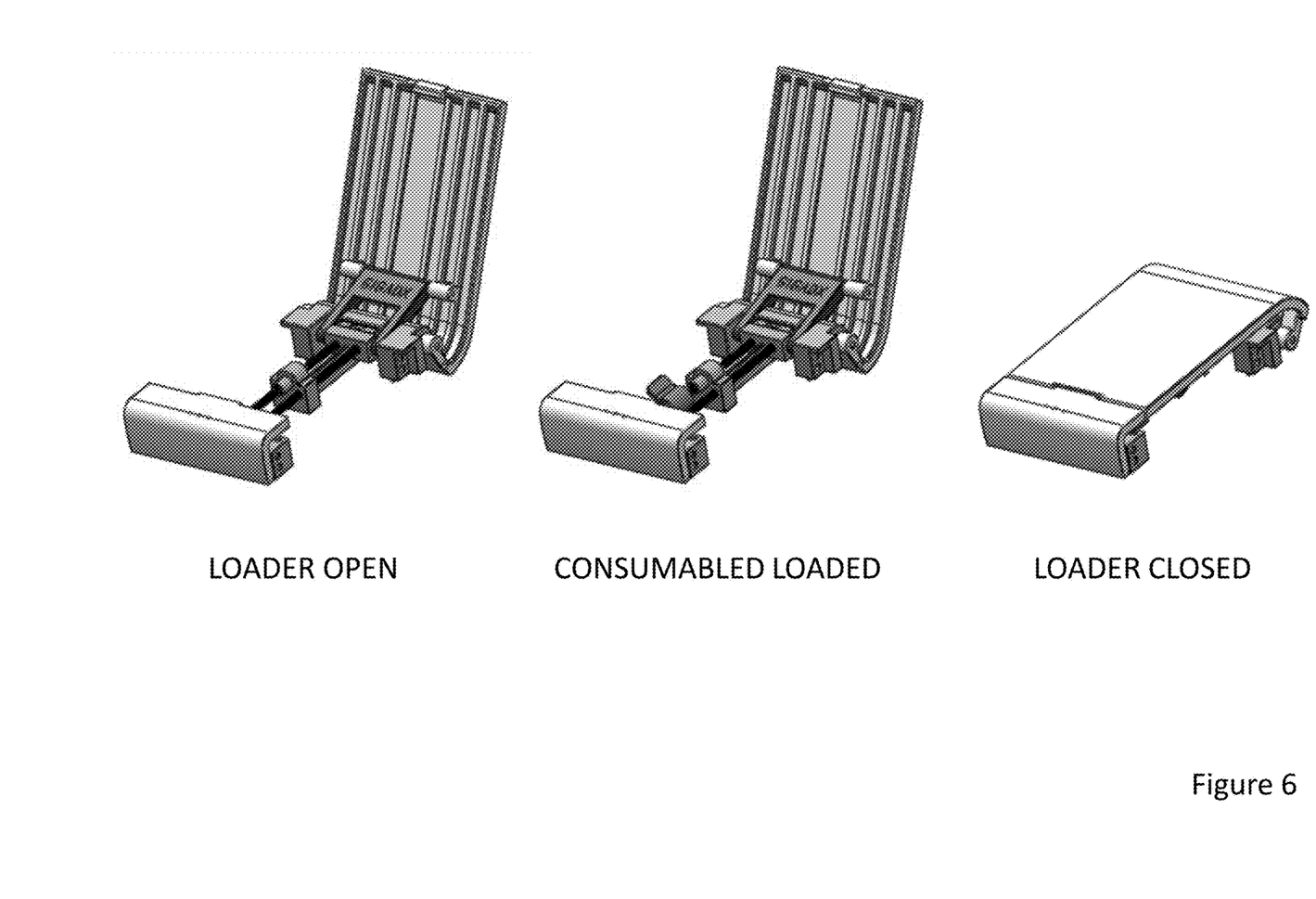
FIG. 6 shows a three-dimensional view of the loader of FIGS. 4 and 5 in its various states.

The embodiment of the mechanical sample loader illustrated in FIGS. 4-6 is based on a crank-slider mechanism with a latch. As shown in FIG. 5, the sample loader has three different states. The first state is closed without consumable. In this state, the plunger forms a seal with the gasket in the receptacle. The second state is closed with the consumable. In this state, the plunger forms a seal to the back of the consumable and the front end of the consumable forms a seal with the gasket in the receptacle. The third state is open with the consumable. In this state, the door is open and allows for the insertion and removal of the capillary To operate the loader, the user presses the latch, which is spring-loaded, and the door opens. While the door is opening, the plunger translates along the rails, creating an opening for the consumable to be loaded or removed. When the door is closed, the mechanism is protected. When the door is open, the consumable and consumable receptacle can be accessed. When the latch is pressed in the system, the spring force in the system opens the door. This allows for one-handed operation. The door remains open when the user inserts or removes the consumable. This is favorable since this allows the user to have one free hand, other than the one loading the consumable. Closing the door moves the plunger towards the front of the crank-slider, thus creating a seal on the back of the consumable or the front gasket.

The loader is based on a mechanical crank-slider. Opening of the door, a rotational movement, directly translates the plunger that makes the seal with the consumable or opposing gasket. The plunger is translated along two rails that guide the motion of the plunger. One advantage of this approach is that the door closes over the mechanical hardware, allowing it to be hidden and thus enhancing user appeal. The travel of the plunger is directly related to the linkages. This is geometrically calculated. Overall, the use of a crank-slider enables the one-handed loading method and increases the user appeal of the instrument.

The plunger is the slide on the loader. It translates along two ⅛" diameter metal rods that serve as alignment rails. The plunger has inlet tubing and an o-ring for sealing to the consumable or opposing gasket. Furthermore, there is a spring platform that pushes on two compression springs. The purpose of the spring platform and springs is to compensate for the presence and absence of the consumable. Essentially, this creates a variable length plunger that can form a seal with or without the consumable. The extended and compressed spring length needs to accommodate for the length of the consumable.

The crank-slider loader needs to form fluid tight seals in the presence and absence of the consumable. The spring-loaded plunger allows this to happen. The plunger has an o-ring or an equivalent means of sealing. This o-ring, with the assistance of the spring force, either presses against the consumable or the gasket in the receptacle on the loader. The receptacle on the front part of the loader has a gasket with a 27 gauge blunt needle passing through its center. The o-ring on the plunger has a larger inner diameter than the gauge of the needle such that it forms a fluid seal around the entrance to the needle when the loader is in its closed position without the consumable. In the presence of the consumable, the plunger's o-ring mates to the back of the consumable. The consumable tip forms a seal against the gasket. The inner diameter of the consumable tip seals around the entrance to the blunt tip needle. In this manner, the double-alignment feature of the consumable is very important.

Elimination of bubbles at the front end of the consumable is important. In order to do this, the loader needs to be primed with fluid in the absence of a consumable. This purges any bubbles from the system and also wets the gasket in the receptacle on the loader. After the flushing, it is important to clamp the entrance and exit tubing to prevent reformation of any bubbles at the interfaces. With this approach, a drop of fluid remains on the gasket after priming and opening. This small drop of fluid then mates with the fluid convexity on the consumable, ensuring a fluid-to-fluid contact. In this scenario, the blunt needle tip is flush with the gasket and there is no requirement of protrusion of the blunt needle tip into the lumen of the capillary. In an alternate scenario, the blunt needle tip can protrude beyond the plane of the gasket and protrude into the lumen of the capillary. In this manner, the volume of the needle displaces any air at the tip of the capillary. This approach is suitable if there is a small amount of air at the tip of the consumable. The presence of the blunt needle tip in the lumen, however, creates a small dead volume that may not be desirable.

A latch is utilized to lock the door in place. The latch prevents inadvertent opening of the door. The latch needs to be pressed in order for the door to open. The latch is displaced when the door is pressed down. The latch meets the requirement of using a single hand opening and closing the device. Two torsion springs control the movement of the latch. They return the latch to its original position after the latch is pressed. The latch should be in its neutral position when the door is closed. This means that the latch can be able to withstand the natural opening force of the door due to the springs in the plunger.

EQUIVALENTS

Those skilled in the art will recognize, or be able to ascertain using no more than routine experimentation and/or engineering, many equivalents to the specific embodiments of the invention described herein. The scope of the present invention is not intended to be limited to the above Description, but rather is as set forth in the claims that follow.

The invention claimed is:

1. A consumable for loading a sample, the consumable comprising:
   a body having a sample loading end and a different exit end;
   a capillary for holding a sample, the capillary open at both the sample loading end and the exit end and providing a fluid pathway through the body from the sample loading end to the exit end;
   an inner alignment feature disposed within the body for aligning the consumable with a loader, the inner alignment feature having an outer surface not in contact with the capillary; and
   an outer alignment feature for aligning the consumable with the loader, the outer alignment feature having an inner surface facing the outer surface of the inner alignment feature, wherein the outer surface of the inner alignment feature is concentrically encompassed by the inner surface of the outer alignment feature.

2. The consumable of claim 1, wherein the body is cylindrical and the outer alignment feature is the cylindrical shape of the body.

3. The consumable of claim 1 further comprising a tab that extends from the body.

4. The consumable of claim 1 further comprising a loading region connected to the capillary for loading the capillary, wherein the loading region is larger than the capillary.

5. The consumable of claim 4 wherein the capillary is concentric with the inner alignment feature and the outer alignment feature.

6. The consumable of claim 4 further comprising an air pocket connecting the capillary and the loading region.

7. The consumable of claim 4 wherein the capillary is tapered.

8. The consumable of claim 1 wherein the body is fabricated from a transparent material.

9. The consumable of claim 1 wherein the inner alignment feature concentrically encompasses the capillary.

10. The consumable of claim 1, wherein the sample loading end has a first diameter and the sample exit end has a second diameter, and wherein ratio of the size of the first diameter to the size of the second diameter is no larger than 3:1.

11. The consumable of claim 1, wherein the diameter of the capillary is no larger than 0.060".

12. The consumable of claim 11, wherein the diameter of the capillary is between 0.020" and 0.060".

13. The consumable of claim 1, wherein the consumable is configured to form a fluid seal at the sample loading end and the different exit end during operation.

* * * * *